United States Patent [19]

Regel et al.

[11] Patent Number: 4,621,095
[45] Date of Patent: Nov. 4, 1986

[54] SUBSTITUTED TERT.-BUTANOL DERIVATIVES AND ANTIMYCOTIC AGENTS CONTAINING THESE COMPOUNDS

[75] Inventors: Erik Regel, Wuppertal; Karl H. Büchel, Burscheid; Manfred Plempel, Haan, all of Fed. Rep. of Germany

[73] Assignee: Bayer Aktiengesellschaft, Leverkusen, Fed. Rep. of Germany

[21] Appl. No.: 522,423

[22] Filed: Aug. 11, 1983

[30] Foreign Application Priority Data

Sep. 2, 1982 [DE] Fed. Rep. of Germany ....... 3232647

[51] Int. Cl.$^4$ ..................... A01N 43/50; A01N 43/56; A01N 43/653; C07D 401/06
[52] U.S. Cl. .................................. 514/383; 514/397; 514/399; 514/406; 548/262; 548/336; 548/341; 548/374; 548/378; 549/552; 549/556; 549/559; 549/560; 549/563; 564/442; 564/501; 564/503; 568/55; 568/58; 568/645; 568/656

[58] Field of Search ............... 548/262, 336, 341, 374; 424/269, 273 R; 514/383, 397, 406

[56] References Cited

U.S. PATENT DOCUMENTS 4,416,682 11/1983 Worthington ..................... 548/336

FOREIGN PATENT DOCUMENTS 0040345 11/1981 European Pat. Off. ............ 548/262
0059894 9/1982 European Pat. Off. ............ 548/262
0061835 10/1982 European Pat. Off. ............ 548/262

Primary Examiner—Alton D. Rollins
Attorney, Agent, or Firm—Sprung, Horn, Kramer & Woods

[57] ABSTRACT

The invention relates to bis-azolyl-substituted t-butanol derivatives defined herein under formula (I) and their use as antimycotic agents. Included in the invention are compositions containing said t-butanol derivatives and methods for using said derivatives and compositions containing them for their antimycotic activity.

16 Claims, No Drawings

SUBSTITUTED TERT.-BUTANOL DERIVATIVES AND ANTIMYCOTIC AGENTS CONTAINING THESE COMPOUNDS

The present invention relates to substituted tert.-butanol derivatives, processes for their preparation and antimycotic agents containing these compounds.

It has already been disclosed that hydroxypropylimidazoles, such as, for example, 2-(4-biphenylyl)-1-(2,4-dichlorophenyl)-3-(imidazol-1-yl)-2-propanol, and 1-hydroxymethyl-azole derivatives, such as, for example, 2-(4-chlorophenoxymethyl)-3,3-dimethyl-1-(imidazol-1-yl)-butan-2-ol or 2-(2-methylphenoxymethyl)-3,3-dimethyl-1-(1,2,4-triazol-1-yl)- and -(imidazol-1-yl)-butan-2-ol, and diazolyl-alkanols, such as, for example, 1,3-di-(imidazol-1-yl)-2-(4-chlorophenyl)-2-propanol, have good antimycotic properties.

Substituted tert.-butanol derivatives of the formula

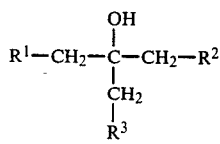

in which
R$^1$, R$^2$ and R$^3$ are identical or different and represent azolyl, optionally substituted phenoxy, optionally substituted phenylthio, alkylthio, alkenyl, alkinyl, optionally substituted phenylacetylenyl, alkylamino, dialkylamino, optionally substituted phenylamino, optionally substituted phenyl-N-alkyl-amino, optionally substituted cycoalkylamino, optionally substituted cycloalkyl-N-alkyl-amino, aminoethoxy, alkylaminoethoxy or dialkylaminoethoxy, and physiologically acceptable acid addition salts thereof, have now been found, having high antimicrobial, particularly high antimycotic activity.

It has furthermore been found that the substituted tert.-butanol derivatives of the formula (I) are obtained by a process in which a nucleophile of the formula (II)

$$R^1-H \qquad (II)$$

in which
R$^1$ has the abovementioned meaning,
(a) is reacted with 2,2-dihalogenomethyloxiranes of the formula (III)

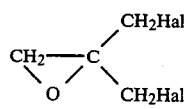

in which
Hal represents halogen,
in the presence of a diluent and in the presence of a an acid-binding agent, or
(b) is reacted with 2-halogenomethyloxiranes of the formula (IV)

in which
R$^2$ and Hal have the abovementioned meaning,
in the presence of a diluent and in the presence of an acid-binding agent, or
(c) is reacted with substituted oxiranes of the formula (V)

in which
R$^2$ and R$^3$ have the abovementioned meaning,
in the presence of a diluent and in the presence of an acid-binding agent.

If desired, an acid can then be added onto the compounds of the formula (I) thus obtained.

The compounds of the formula (I) may have an asymmetric carbon atom, and they may therefore possibly be obtained in the two optical isomer forms.

Racemate mixtures can be separated into the pure racemates in a known manner on the basis of the physicochemical differences of the constituents, for example by chromatography and/or fractional crystallization.

Pure racemates can be resolved according to known methods, for example by recrystallization from an optically active solvent, with the aid of micro-organisms or by reaction with an optically active acid or base which forms salts with the racemic compound and separation of the salts obtained in this manner, for example on the basis of their different solubilities, into the diastereomers from which the antipodes can be liberated by the action of suitable agents. Particularly customary optically active acids are, for example, the d- and l-forms of tartaric acid, di-o-toluyltartaric acid, malic acid, mandelic acid, camphorsulphonic acid or quinic acid. Suitable optically active bases are, for example, optically active α-phenylethylamine, α-(1-naphthyl)-ethylamine, quinine, cinchonidine and brucine. Advantageously, the more active of the two antipodes is isolated.

According to the invention it is however also possible to obtain the end product in the form of pure racemates or optical antipodes by employing starting substances, containing one or more asymmetrical C atoms, in the form of the pure racemates or optical antipodes.

The new substituted tert.-butanol derivatives of the formula (I) have powerful antimycotic properties. Surprisingly, the compounds according to the invention exhibit a better in vivo activity, in particular a therapeutically useful in vivo activity, than the compounds 2-(4-biphenylyl)-1-(2,4-dichlorophenyl)-3-imidazol-1-yl)-2-propanol; 2-(4-chlorophenoxymethyl)-3,3-dimethyl-1-(imidazol-1-yl)-butan-2-ol; 2-(2-methylphenoxymethyl)-3,3-dimethyl-1-(1,2,4-triazol-1-yl)- and -(imidazol-1-yl)-butan-2-ol and 1,3-di-(imidazol-1-yl)-2-(4-chlorophenyl)-2-propanol, which are known from the prior art and are closely related compounds structurally and from the point of view of their action. The substances according to the invention thus represent an enrichment of pharmacy.

The new substituted tert.-butanol derivatives are also interesting intermediates. Thus, for example, the compounds of the formula (I) can be converted into the corresponding ether on the hydroxyl group in the customary manner. Furthermore, acyl or carbamoyl derivatives of the compounds of the general formula (I) can be obtained by reaction with, for example, acyl halides or carbamoyl chlorides in a manner which is known in principle. The term "acyl" as used herein refers particularly to carboxylic acid acyl and also sulfonic acid acyl and especially to $C_1$-$C_4$-alkane-carboxylic acid acyl.

Formula (I) provides a general definition of the substituted tert.-butanol derivatives according to the invention.

Preferred compounds of the formula (I) are those in which (A)

$R^1$ and $R^2$ are identical or different and represent imidazol-1-yl, 1,2,4-triazol-1-yl; 1,2,4-triazol-4-yl or pyrazol-1-yl and $R^3$ represents phenoxy, phenylthio, phenylamino or phenyl-N-alkyl-amino with 1 to 4 carbon atoms in the alkyl part, each radical being optionally monosubstituted, disubstituted or polysubstituted by identical or different substituents, possible substituents on phenyl in each case being: halogen, alkyl with 1 to 6 carbon atoms, alkoxy and alkylthio with in each case 1 to 4 carbon atoms; halogenoalkyl, halogenoalkoxy and halogenoalkylthio with in each case 1 to 4 carbon atoms and 1 to 5 identical or different halogen atoms, such as fluorine and chlorine atoms; cycloalkyl with 5 or 6 carbon atoms; nitro, cyano, hydroxycarbonyl, alkylcarbonyl or alkoxycarbonyl with in each case 1 to 4 carbon atoms in the alkyl part, phenyl or phenoxy which is optionally monosubstituted, disubstituted or polysubstituted by identical or different substituents from the group comprising halogen, nitro, trifluoromethyl and alkyl, with 1 to 2 carbon atoms, the aldehyde group or the oxime or oxime ether radical;

Other preferred compounds of the formula (I) are those in which (B)

$R^1$ and $R^2$ are identical or different and represent imidazol-1-yl; 1,2,4-triazol-1-yl, 1,2,4-triazol-4-yl or pyrazol-1-yl and $R^3$ represents alkylthio with 1 to 12 carbon atoms, alkylamino or dialkylamino with in each case 1 to 4 carbon atoms in each alkyl part, aminoethoxy, alkylaminoethoxy or dialkylaminoethoxy with in each case 1 to 4 carbon atoms in each alkyl part, or cycloalkylamino or cycloalkyl-N-alkylamino with in each case 3 to 7 carbon atoms in the cycloalkyl part and 1 to 4 carbon atoms in the alkyl part and in each case optionally monosubstituted or polysubstituted in the cycloalkyl part by identical or different substituents, possible substituents being: halogen, alkyl with 1 to 4 carbon atoms and alkoxy with 1 to 2 carbon atoms.

Further preferred compounds of the formula (I) are those in which (C)

$R^1$ represents imidazol-1-yl; 1,2,4-triazol-1-yl; 1,2,4-triazol-4-yl or pyrazol-1-yl and $R^2$ and $R^3$ are identical or different and have the meanings given above for $R^3$ under point (A).

Other preferred compounds of the formula (I) are those in which (D)

$R^1$ represents imidazol-1-yl; 1,2,4-triazol-1-yl; 1,2,4-triazol-4-yl or pyrazol-1-yl and $R^2$ and $R^3$ are identical or different and have the meanings given above for $R^3$ under point (B).

Preferred compounds of the formula (I) are likewise those in which (E)

$R^1$, $R^2$ and $R^3$ are identical or different and have the meanings given above for $R^3$ under points (A) and (B).

Finally, preferred compounds of the formula (I) are also those in which (F)

$R^1$, $R^2$ and $R^3$ are identical or different and have the meanings mentioned above for $R^1$ under point (A).

Particularly compounds of the formula (I) are those in which (A)

$R^1$ and $R^2$ are identical or different and represent imidazol-1-yl; 1,2,4-triazol-1-yl; 1,2,4-triazol-4-yl or pyrazol-1-yl, and $R^3$ represent phenoxy, phenylthio, phenylamino or phenyl-N-alkyl-amino with 1 or 2 carbon atoms in the alkyl part, each radical optionally being monosubstituted or di- or tri-substituted by identical or different substituents, possible substituents on the phenyl in each case being: fluorine, chlorine, bromine, methyl, ethyl, isopropyl, tert.-butyl, 2-methyl-but-2-yl, methoxy, ethoxy, methylthio, trifluoromethylthio, cyclohexyl, nitro, cyano, hydroxycarbonyl, methylcarbonyl, methoxycarbonyl, ethoxycarbonyl, or phenyl or phenoxy, in each case optionally monosubstituted or di- or tri-substituted by identical or different substituents from the groups comprising chlorine, nitro, trifluoromethyl and methyl, or the aldehyde group, hydroxyiminoethyl or methoxyiminomethyl.

Other particularly preferred compounds of the formula (I) are those in which (B)

$R^1$ and $R^2$ are identical or different and represent imidazol-1-yl; 1,2,4-triazol-1-yl; 1,2,4-triazol-4-yl or pyrazol-1-yl and $R^3$ represents methylthio, ethylthio, buthylthio or dodecylthio, or alkylamino or dialkylamino with in each case 1 or 2 carbon atoms in each alkyl part, or aminoethoxy, alkylaminoethoxy or dialkylaminoethoxy with in each case 1 or 2 carbon atoms in each alkyl part, or cyclopropylamino, cyclopentylamino, cyclohexylamino, cyclopropyl-N-methyl-amino, cyclopentyl-N-methyl-amino or cyclohexyl-N-methyl-amino, in each case optionally mono-, di- or tri-substituted in the cycloalkyl part by identical or different substituents, possible substituents being: chlorine, bromine, methyl, ethyl, isopropyl and methoxy.

Particularly preferred compounds of the formula (I) are furthermore those in which (C')
R¹ represents imidazol-1-yl; 1,2,4-triazol-1-yl; 1,2,4-triazol-4-yl or pyrazol-1-yl and
R² and R³ are identical or different and have the meanings mentioned above for R³ under point (A').

Further particularly preferred compounds of the formula (I) are those
in which
(D')
R¹ represents imidazol-1-yl; 1,2,4-triazol-1-yl; 1,2,4-triazol-4-yl or pyrazol-1-yl and
R² and R³ are identical or different and have the meanings given above for R³ under point (B')

Particularly preferred compounds of the formula (I) are likewise those
in which
(E')
R¹, R² and R³ are identical or different and have the meanings given above for R³ under points (A') and (B').

Finally, particularly preferred compounds of the formula (I) are also those
in which
(F')
R¹, R² and R³ are identical or different and have the meanings given above for R¹ under point (A').

The following compounds of the formula (I) may be mentioned specifically, in addition to the compounds mentioned in the preparation examples:

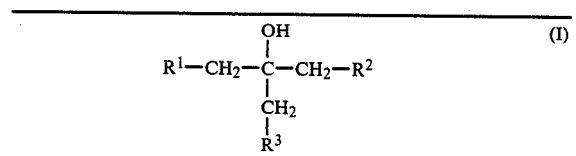
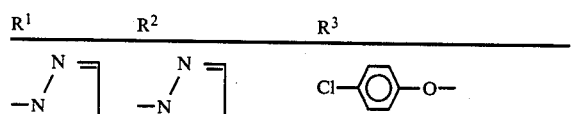
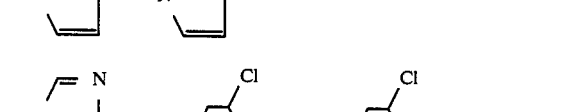
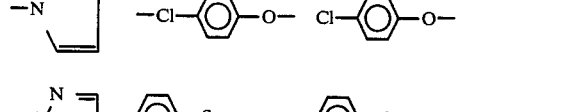
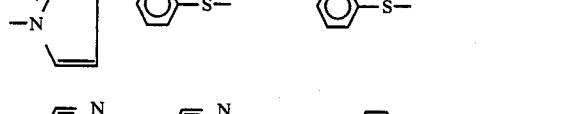
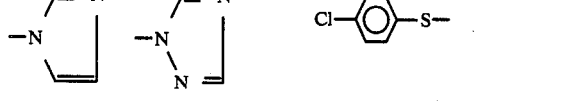
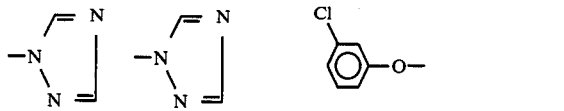
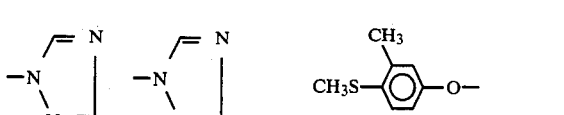

-continued

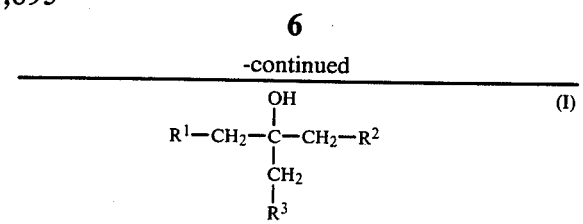
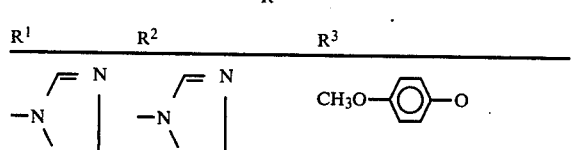
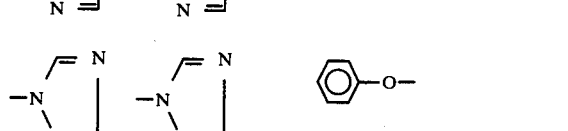
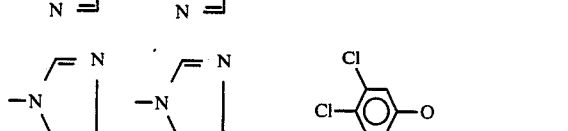
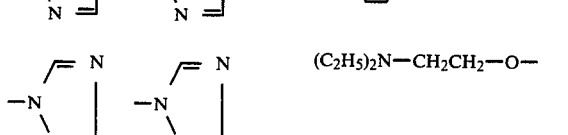
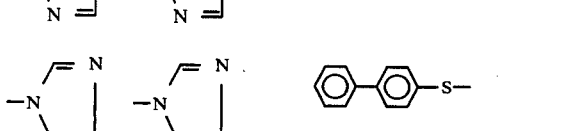
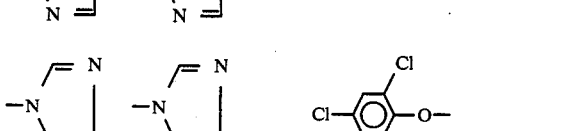
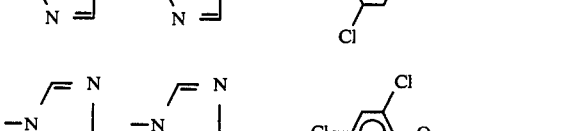
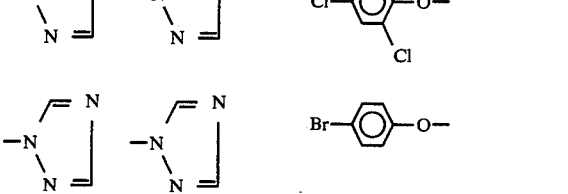

If, for example, 2,2-di(chloromethyl)-oxirane and 1,2,4-triazole are used as the starting substances, the course of the reaction in process (a) according to the invention can be represented by the following equation:

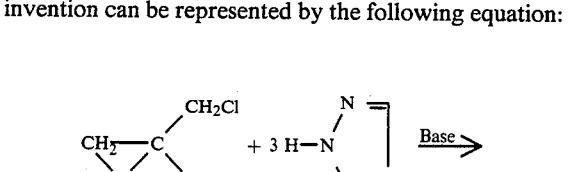

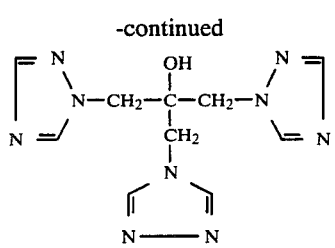

If, for example, 2-chloromethyl-2-(4-chlorophenoxymethyl)-oxirane and 1,2,4-triazole are used as the starting substances, the course of the reaction in process (b) according to the invention can be represented by the following equation:

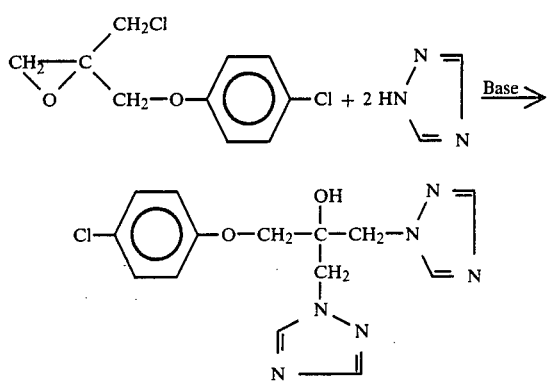

If, for example, 2,2-di(2,4-dichlorophenoxymethyl)-oxirane and 1,2,4-triazole are used as the starting substances, the course of the reaction in process (c) according to the invention can be represented by the following equation:

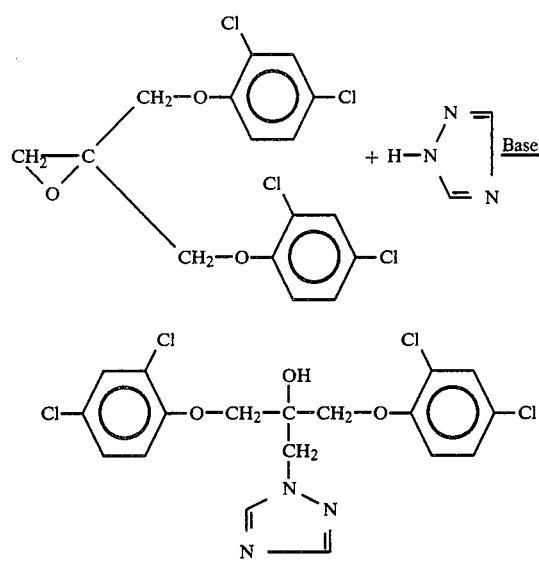

Formula (II) provides a general definition of the nucleophiles to be used as starting substances for processes (a), (b) and (c) according to the invention. In this formula, $R^1$ preferably represents those radicals which have already been mentioned as preferred for this substituent in connection with the description of the substances of the formula (I) according to the invention.

The nucleophiles of the formula (II) are generally known compounds of organic chemistry.

Formula (III) provides a general definition of the 2,2-dihalogenomethyloxiranes also to be used as starting substances for process (a) according to the invention. In this formula, Hal preferably represents chlorine or bromine.

The 2,2-dihalogenomethyloxiranes of the formula (III) are known (compare Beilstein, E III (1), pages 1587–1588), or they can be obtained in a known manner, in which 3-halogeno-2-halogenomethylpropenes of the formula (VI)

in which
Hal has the abovementioned meaning,
are either first reacted with a tert.-butoxyhalide to give 1,3-dihalogeno-2-halogenomethyl-2-propanols of the formula (VII)

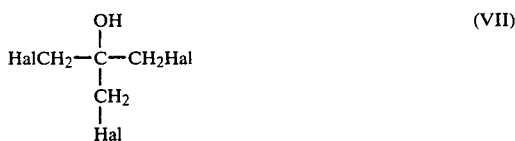

in which
Hal has the abovementioned meaning,
and these are then epoxidised in the presence of calcium hydroxide to give the desired 2,2-dihalogenomethyloxiranes of the formula (III) (in this context, compare also Beilstein, E III (1), pages 1587–1588); or epoxidised directly in the presence of peracids, such as, for example, peracetic acid, perpropionic acid or m-chloroperbenzoic acid, to give the desired 2,2-dihalogenomethyloxiranes of the formula (III).

Formula (IV) provides a general definition of the 2-halogenomethyloxiranes also to be used as starting substances for process (b) according to the invention. In this formula, $R^2$ preferably represents those radicals which have already been mentioned as preferred for this substituent in connection with the description of the substances of the formula (I) according to the invention. Hal preferably represents chlorine or bromine.

The 2-halogenomethyloxiranes of the formula (IV) are not yet known. However, they can be obtained in a generally customary manner, in which either 2,2-dihalogenomethyloxiranes of the formula (III) are reacted with a nucleophile of the formula (II); or 3-halogeno-2-halogenomethyl-propenes of the formula (VI) are first reacted with a nucleophile of the formula (II), if appropriate in the form of an alkali metal salt, to give propenes of the formula (VIII)

in which
Hal and $R^1$ have the abovementioned meaning, and these are then epoxidised in the presence of peracids to give the desired 2-halogenomethyloxiranes of the formula (IV).

Formula (V) provides a general definition of the oxiranes also to be used as starting substances for process (c) according to the invention. In this formula, $R^2$ and $R^3$ preferably represent those radicals which have already been mentioned as preferred for the substituent in connection with the description of the substances of the formula (I) according to the invention.

The substituted oxiranes of the formula (V) are not yet known. However, they can be obtained in a generally customary manner, in which either 2,2-dihalogenomethyloxiranes of the formula (III) are reacted with a nucleophile of the formula (II); or 3-halogeno-2-halogenomethyl-propenes of the formula (VI) are reacted with a nucleophile of the formula (II), if appropriate in the form of an alkali metal salt, to give propenes of the formula (IX)

in which $R^1$ has the abovementioned meaning, and these are then epoxidised in the presence of peracids to give the desired oxiranes of the formula (V); or ketones of the formula (X)

in which $R^1$ and $R^2$ have the abovementioned meaning, are epoxidised with dimethylsulphonium methylide in a manner which is known per se.

Preferred possible diluents for processes (a), (b) and (c) according to the invention are inert organic solvents. These include, preferably, ketones, such as, in particular, acetone and methyl ethyl ketone; nitriles, such as, in particular, acetonitrile; alcohols, such as, in particular, ethanol and isopropanol; ethers, such as, in particular, tetrahydrofuran or dioxane; formamides, such as, in particular, dimethylformamide; aromatic and halogenated hydrocarbons, such as toluene and chlorobenzene.

If necessary, processes (a), (b) and (c) according to the invention are carried out in the presence of acid-binding agents. All the inorganic or organic acid-binding agents which can usually be used may be added, such as alkali metal hydroxides and alkali metal carbonates, for example sodium hydroxide and potassium hydroxide and sodium carbonate and potassium carbonate; or ammonia or such as lower tertiary alkylamine, preferably having 1 to 4 carbon atoms in each alkyl group, $C_4$-$C_7$-cycloalkylamines or aralkylamines, for example triethylamine, N,N-dimethyl-$C_4$-$C_7$-cyclohexylamine, dicyclohexylamine or N,N-dimethylbenzylamine, and furthermore pyridine and diazobicyclooctane, as well as an appropriate excess of imidazole or triazole.

The reaction temperatures can be varied within a substantial range in carrying out processes (a), (b) and (c) according to the invention. In general, the reaction is carried out between about 20° and about 150° C., preferably at 20° to 120° C.

In carrying out processes (a), (b) and (c) according to the invention, in each case the stoichiometrically required amount up to a 3-molar excess required amount of nucleophile of the formula (II) and the stoichiometric amounts up to a 2-molar excess of acid-binding agent are used per mol of oxiranes of the formulae (III), (IV) and (V). The compounds of the formula (I) are isolated in the customary manner.

All the physiologically acceptable acids can be used for the preparation of acid addition salts of the compounds of the formula (I). These include, preferably, the hydrogen halide acids, such as, for example, hydrochloric acid and hydrobromic acid, in particular hydrochloric acid, and furthermore phosphoric acid, nitric acid, sulphuric acid, monofunctional and bifunctional carboxylic acids and hydroxycarboxylic acids, such as, for example, acetic acid, maleic acid, succinic acid, fumaric acid, tartaric acid, citric acid, salicylic acid, sorbic acid and lactic acid, and sulphonic acids, such as, for example, p-toluenesulphonic acid and 1,5-naphthalenedisulphonic acid.

The salts of compounds of the formula (I) can be obtained in a simple manner by customary salt formation methods, for example by dissolving a compound of the formula (I) in a suitable inert solvent and adding the acid, for example hydrochloric acid, and they can be isolated in a known manner, for example by filtration, and if necessary purified by washing with an inert organic solvent.

Certain compounds of the formula (I) can also be obtained by a process in which di(halogenomethyl)-carbinols of the formula (XI)

in which

Hal has the abovementioned meaning and $R^4$ represents optionally substituted phenylthio, alkylthio, alkylamino, dialkylamino, optionally substituted phenylamino, optionally substituted phenyl-N-alkyl-amino, optionally substituted cycloalkylamino or optionally substituted cycloalkyl-N-alkylamino, under the conditions of process (a). In the carbinols of formula (XI), in defining $R^4$, —unless otherwise specified—each alkyl moiety preferably contains 1 to 6 (especially 1 to 4) carbon atoms and cycloalkyl preferably contains 4 to 7 (especially 5 or 6) ring members. Optional substituents on the phenyl or cycloalkyl moieties include $C_1$-$C_4$-alkyl or alkoxy or halogen (especially bromine, chlorine or fluorine).

The compounds of the formula (I) according to the invention and their physiologically acceptable acid addition salts display antimicrobial actions, in particular powerful antimycotic action in warm-blooded anims. They possess a very broad antimycotic action spectrum, especially against dermatophytes and blastomyces as well as biphase fungi, for example against species of Candida, such as *Candida albicans*, species of Epidermophyton, such as *Epidermophyton floccosum*, species of Aspergillus, such as *Aspergillus niger* and *Aspergillus fumigatus*, species of Trichophyton, such as *Trichophy-*

*ton mentagrophytes,* species of Microsporon, such as *Microsporon felineum* and species of Torulopsis, such as *Torulopsis glabrata.* The listing of these micro-organisms in no way implies a limitation of the germs which can be combated but is only of illustrative character.

The present invention includes pharmaceutical formulations which, in addition to non-toxic, inert pharmaceutically suitable excipients, contain one or more active compounds according to the invention, or which consist of one or more active compounds according to the invention, as well as processes for the preparation of these formulations.

The present invention also includes pharmaceutical formulations in dosage units. This means that the formulations are in the form of individual parts, for example tablets, dragees, capsules, pills, suppositories and ampoules, of which the content of active compound corresponds to a fraction of a multiple of an individual dose. The dosage units can contain, for example, 1, 2, 3 or 4 individual doses or ½, ⅓ or ¼ of an individual dose. An individual dose preferably contains the amount of active compound which is given in one administration and which usually corresponds to a whole, a half, a third or a quarter of a daily dose.

By non-toxic, inert pharmaceutically suitable excipients there are to be understood solid, semi-solid or liquid diluents, fillers and formulations auxiliaries of every kind.

Tablets, dragees, capsules, pills, granules, suppositories, solutions, suspensions and emulsions, pastes, ointments, gels, creams, lotions, powders and sprays may be mentioned as preferred pharmaceutical formulations.

Tablets, dragees, capsules, pills and granules can contain the active compound or compounds alongside the customary excipients, such as (a) fillers and extenders, for example starches, lactose, sucrose, glucose, mannitol and silica, (b) binders, for example carboxymethylcellulose, alginates, gelatin and polyvinylpyrrolidone, (c) humectants, for example glycerol, (d) disintegrating agents, for example agar-agar, calcium carbonate and sodium bicarbonate, (e) solution retarders, for example paraffin, and (f) resorption accelerators, for example quaternary ammonium compounds, (g) wetting agents, for example cetyl alcohol and glycerol monostearate, (h) adsorbents, for example kaolin and bentonite, and (i) lubricants, for example talc, calcium stearate and magnesium stearate and solid polyethylene glycols, or mixtures of the compounds listed under (a) to (i).

The tablets, dragees, capsules, pills and granules can be provided with the customary coatings and shells, optionally containing opacifying agents, and can also be of such composition that they release the active compound or compounds only, or preferentially, in a certain part of the intestinal tract, optionally in a delayed manner, examples of embedding compositions which can be used being polymeric substances and waxes.

The active compound or compounds, optionally together with one or more of the abovementioned excipients can also be a micro-encapsulated form.

Suppositories can contain, in addition to the active compound or compounds, the customary water-soluble or water-insoluble excipients, for example polyethylene glycols, fats, for example cacao fat, and higher esters (for example $C_{14}$-alcohol with $C_{16}$-fatty acid), or mixtures of these substances.

Ointments, pastes, creams and gels can contain, in addition to the active compound or compounds, the customary excipients, for example animal and vegetable fats, waxes, paraffins, starches, tragacanth, cellulose derivatives, polyethylene glycols, silicones, bentonites, silica, talc and zinc oxide, or mixtures of these substances.

Powders and sprays can contain, in addition to the active compound or compounds, the customary excipients, for example lactose, talc, silica, aluminium hydroxide, calcium silicate and polyamide powders or mixtures of these substances. Sprays can additionally contain the customary propellants, for example chlorofluorohydrocarbons.

Solutions and emulsions can contain, in addition to the active compound or compounds, the customary excipients, such as solvents, solubilising agents and emulsifiers, for example water, ethyl alcohol, isopropyl alcohol, ethyl carbonate, ethyl acetate, benzyl alcohol, benzyl benzoate, propylene glycol, 1,3-butylene glycol, dimethylformamide, oils, especially cottonseed oil, groundnut oil, maize germ oil, olive oil, castor oil and sesame oil, glycerol, glycerol-formal, tetrahydrofurfuryl alcohol, polyethylene glycols and fatty acid esters of sorbitane, or mixtures of these substances.

For parenteral administration, the solutions and emulsions can also be in a sterile form which is isotonic with blood.

Suspensions can contain, in addition to the active compound or compounds, the customary excipients, such as liquid diluents, for example water, ethyl alcohol or propylene glycol, suspending agents, for example ethoxylated isostearyl alcohols, polyoxyethylene sorbitol esters and sorbitane esters, micro-crystalline cellulose, aluminium metahydroxide, bentonite, agar-agar and tragacanth, or mixtures of these substances.

The formulation forms mentioned can also contain colorants, preservatives and additives which improve the odour and flavour, for example peppermint oil and eucalyptus oil, and sweeteners, for example saccharin.

The therapeutically active compounds should preferably be present in the abovementioned pharmaceutical formulations in a concentration of about 0.1 to 99.5, preferably of about 0.5 to 95, % by weight of the total mixture.

The abovementioned pharmaceutical formulations can also contain other pharmaceutical active compounds in addition to the active compounds according to the invention.

The abovementioned pharmaceutical formulations are prepared in the customary manner according to known methods, for example by mixing the active compound or compounds with the excipient or excipients.

The present invention also includes the use of the active compounds according to the invention, and of pharmaceutical formulations which contain one or more active compounds according to the invention, for the treatment of the above mentioned diseases.

The active compounds or the pharmaceutical formulations can be administered locally, orally, parenterally, intraperitoneally and/or rectally, preferably parenterally, and in particular intravenously.

In general, it has proved advantageous in medicine, to administer the active compound or compounds according to the invention in total amounts of about 10 to about 300, preferably 50 to 200, mg/kg of body weight every 24 hours, optionally in the form of several individual administrations, in order to achieve the desired results.

However, it can be necessary to deviate from the dosages mentioned, and in particular to do so as a function of the species and the body weight of the subject to be treated, the nature and severity of the disease, the nature of the formulation and of the administration of the medicament and the time or interval over which the administration takes place. Thus it can in some cases suffice to manage with less than the abovementioned amount of active compound, whilst in other cases the abovementioned amount of active compound must be exceeded. The particular optimum dosage required and the type of administration of the active compounds can easily be determined by anyone skilled in the art on the basis of his expert knowledge.

Preparation Examples

EXAMPLE 1 AND 2

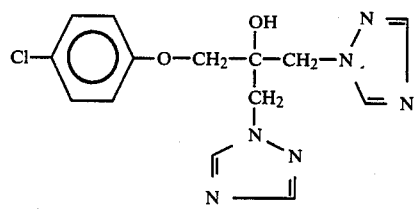
(Example 1)

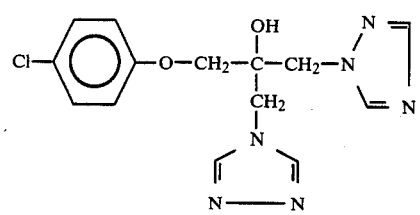
(Example 2)

(process b)

9.4 g (0.04 mol) of 2-chloromethyl-2-(4-chlorophenoxymethyl)-oxirane are added dropwise to a mixture of 13.6 g (0.2 mol) of 1,2,4-triazole and 13.8 g (0.1 mol) of potassium carbonate in 200 ml of acetone, whilst stirring. The mixture is stirred at room temperature for 15 hours and then under reflux for 22 hours. Thereafter, the reaction mixture is filtered cold and the filtrate is concentrated in vacuo. The oily residue is dissolved in chloroform and the solution is washed with water, dried over sodium sulphate and purified chromatographically (silica gel 60 Merck, chloroform/methanol=20/1). 5.8 g (43% of theory) of 2-(4-chlorophenoxymethyl)-1,3-di-(1,2,4-triazol-1-yl)-2-hydroxypropane of melting point 99° C. (Example 1) and 2.0 g (15% of theory) of 2-(4-chlorophenoxymethyl)-2-hydroxy-1-(1,2,4-triazol-1-yl)-3-(1,2,4-triazol-4-yl)-propane (Example 2) of melting point 160° C. are obtained.

PREPARATION OF THE STARTING SUBSTANCE

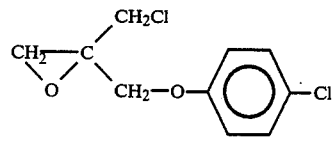

(1st variant)

12.85 g (0.1 mol) of 4-chlorophenol in 50 ml of acetone are added dropwise to a mixture of 14.1 g (0.1 mol) of 2,2-di(chloromethyl)-oxirane and 13.8 g (0.1 mol) of potassium carbonate in 200 ml of acetone. The mixture is heated under reflux for 18 hours, left to cool and filtered. The filtrate is concentrated in vacuo, the residue is dissolved in chloroform and the solution is washed with water, dried over sodium sulphate and concentrated. Purification of the residue by distillation gives 7.6 g (32.5% of theory) of 2-chloromethyl-2-(4-chlorophenoxymethyl)-oxirane of boiling point 150° C./0.5 mbar.

(2nd variant)

0.5 mol of sodium 4-chlorophenolate in acetonitrile are added dropwise to a solution of 125 g (1 mol) of 3-chloro-2-chloromethylpropene in 50 ml of acetonitrile. After addition of 0.5 g of sodium iodide, the reaction mixture is heated under reflux for 12 hours and is then filtered cold. The filtrate is concentrated in vacuo. The residue is dissolved in methylene chloride and the solution is washed with water, dried over sodium sulphate and concentrated. 58.6 g of about 60% pure 2-chloromethyl-3-(4-chlorophenoxy)-propene are obtained and are dissolved in 500 ml of methylene chloride, and 43 g (0.25 mol) of 3-chloroperbenzoic acid are added.

The mixture is stirred at room temperature for 24 hours and filtered. The filtrate is washed with aqueous 10% strength sodium thiosulphate solution, dried over sodium sulphate and concentrated in vacuo. Purification of the residue by distillation gives 30 g (12.9% of theory) of 2-chloromethyl-2-(4-chlorophenoxymethyl)-oxirane of refractive index $n_D^{20}$ 1.5465.

EXAMPLE 3, 4 AND 5

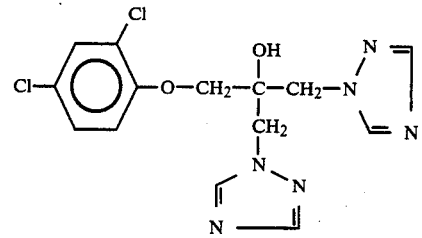
(Example 3)

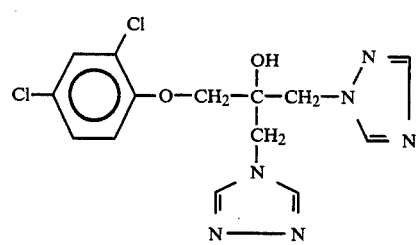
(Example 4)

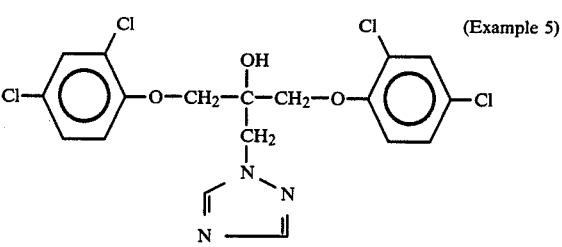
(Example 5)

(Processes b and c)

23.5 g of a mixture of 2-chloromethyl-2-(2,4-dichlorophenoxymethyl)-oxirane and 2,2-bis(2,4-dichlorophenoxymethyl)-oxirane are added dropwise to a solution of 20.7 g (0.3 mol) of 1,2,4-triazole and 13.8 g (0.1 mol) of potassium carbonate in 200 ml of acetone. The reaction mixture is stirred under reflux for 20 hours. Thereafter, the mixture is filtered cold and the filtrate is concentrated in vacuo. The residue is dissolved in chloroform and the solution is washed with water, dried over sodium sulphate and purified and separated by chromatography (silica gel 60 Merck). The column is first eluted with chloroform. The eluate thereby obtained is concentrated by distilling off the solvent, and the residue is stirred with diethyl ether. 4.8 g of 1,3-bis-(2,4-dichlorophenoxy)-2-hydroxy-2-(1,2,4-triazol-1-yl-methyl)-propane (Example 5) of melting point 136° C. are obtained.

The column is then eluted with chloroform/methanol: 40/1. The eluate thereby obtained is concentrated by distilling off the solvent, and the residue is stirred with acetonitrile. 3.9 g of 2-(2,4-dichlorophenoxymethyl)-1,3-di(1,2,4-triazol-1-yl)-2-hydroxy-propane (Example 3) of melting point 138° C. are obtained.

Finally, the column is eluted with chloroform/methanol: 20/1. The eluate thereby obtained is concentrated by distilling off the solvent, and the residue is stirred with acetonitrile. 3.7 g of 2-(2,4-dichlorophenoxymethyl)-2-hydroxy-1-(1,2,4-triazol-1-yl)-3-(1,2,4-triazol-4-yl)-propane (Example 4) of melting point 182° C. are obtained.

PREPARATION OF THE STARTING SUBSTANCES

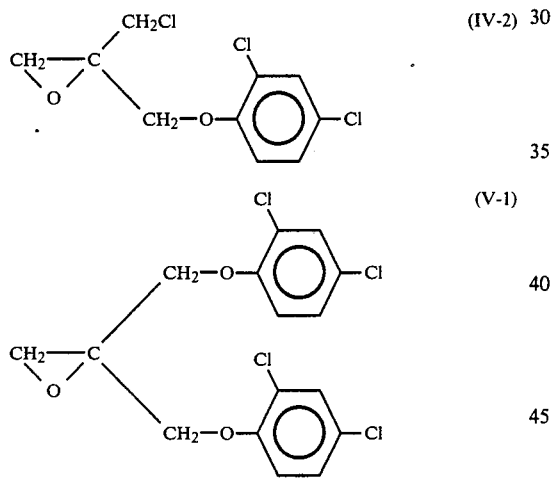

A mixture of 14.1 g (0.1 mol) of 2,2-di(chloromethyl)-oxirane, 13.8 g (0.1 mol) of potassium carbonate and 16.3 g (0.1 mol) of 2,4-dichlorophenol in 150 ml of acetone is heated to 60° C. for 15 hours and is then filtered cold, and the filtrate is concentrated in vacuo. The residue is taken up in methylene chloride and the solution is washed with water, dried over sodium sulphate and concentrated. 23.5 g of an oily mixture which, on the basis of determination by gas chromatography, contains 47% of 2-chloromethyl-2-(2,4-dichlorophenoxymethyl)-oxirane (Example IV-2) and 24.9% of 2,2-bis(2,4-dichlorophenoxymethyl)-oxirane (Example V-1), in addition to 14.9% of unreacted 2,2-di(chloromethyl)-oxirane, are obtained.

If necessary, this mixture can be separated by chromatography, 2-chloromethyl-2-(2,4-dichlorophenoxymethyl)-oxirane (Example IV-2) of refractive index $n_D^{20}$ 1.5568 and 2,2-bis-(2,4-dichlorophenoxymethyl)-oxirane (Example V-1) of melting point 64° C. being obtained.

EXAMPLE 6

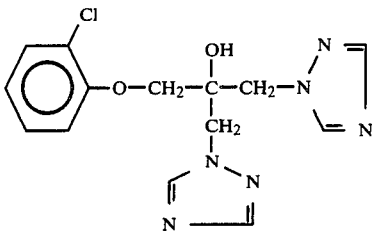

(Process b)

7.1 g (55% of theory) of 2-(2-chlorophenoxymethyl)-1,3-di(1,2,4-triazol-1-yl)-2-hydroxy-propane of melting point 95° C. are obtained according to Example 1/2 from 8.9 g (0.038 mol) of 2-chloromethyl-2-(2-chlorophenoxymethyl)-oxirane, 5 g (0.038 mol) of potassium carbonate and 6.9 g (0.1 mol) of 1,2,4-triazole in 200 ml of acetone, after purification of the reaction product by chromatography (silica gel 60, Merck, chloroform/methanol=40/1).

PREPARATION OF THE STARTING SUBSTANCE

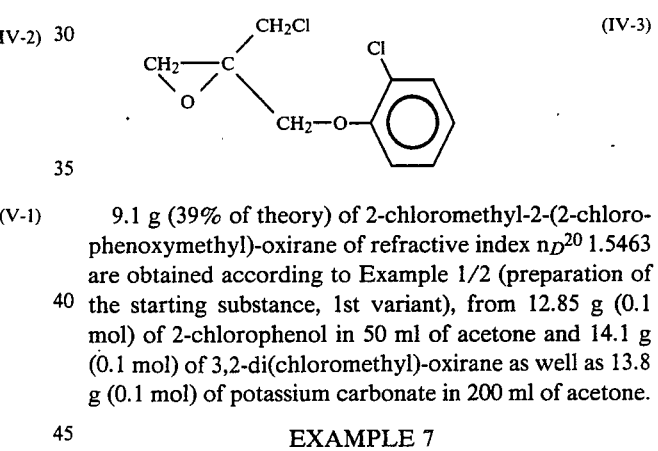

9.1 g (39% of theory) of 2-chloromethyl-2-(2-chlorophenoxymethyl)-oxirane of refractive index $n_D^{20}$ 1.5463 are obtained according to Example 1/2 (preparation of the starting substance, 1st variant), from 12.85 g (0.1 mol) of 2-chlorophenol in 50 ml of acetone and 14.1 g (0.1 mol) of 3,2-di(chloromethyl)-oxirane as well as 13.8 g (0.1 mol) of potassium carbonate in 200 ml of acetone.

EXAMPLE 7

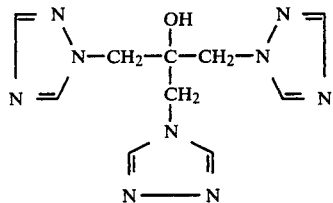

(Process a)

28.2 g (0.2 mol) of 2,2-di(chloromethyl)-oxirane are added dropwise to a mixture of 82.5 g (1.2 mol) of 1,2,4-triazole and 82.5 g (0.6 mol) of potassium carbonate in 400 ml of acetone, whilst stirring. The reaction mixture is stirred under reflux for 50 hours and filtered and the filtrate is concentrated in vacuo. The oily residue is chromatographed (silica gel 60, Merck, chloroform/methanol=20/1). 5.9 g (10.7% of theory) of 1,3-di-(1,2,4-triazol-1-yl)-2-hydroxy-2-(1,2,4-triazol-4-yl-methyl)-propane of melting point 220° C. are obtained.

EXAMPLE 8 AND 9

(Example 8)
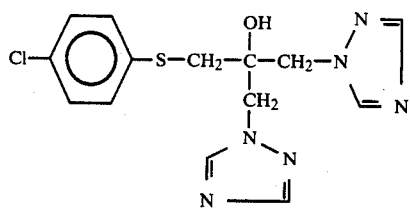

(Example 9)
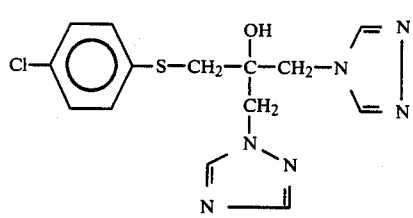

(Process b)

12.1 g (57.5% of theory) of 2-(4-chlorophenylthiomethyl)-1,3-di(1,2,4-triazol-1-yl)-2-hydroxy-propane (Example 8) of melting point 150° C. and 4.6 g (22% of theory) of 2-(4-chlorophenylthiomethyl)-2-hydroxy-1-(1,2,4-triazol-1-yl)-3-(1,2,4-triazol-4-yl)-propane (Example 9) of melting point 186° C. are obtained according to Example 1/2, from 14.8 g (0.06 mol) of 2-chloromethyl-2-(4-chlorophenylthiomethyl)-oxirane, 8.3 g (0.12 mol) of 1,2,4-triazole and 8.3 g (0.06 mol) of potassium carbonate in 200 ml of acetone.

PREPARATION OF THE STARTING PRODUCT

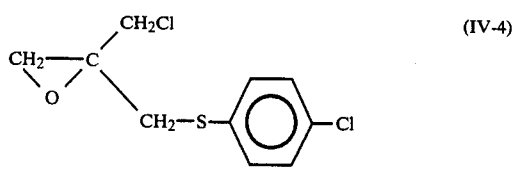
(IV-4)

5.4 g (0.1 mol) of sodium methylate are introduced in portions into a mixture of 16.9 g (0.12 mol) of 2,2-di(-chloromethyl)-oxirane and 14.5 g (0.1 mol) of 4-chlorothiophenol in 200 ml of acetonitrile. The reaction mixture is subsequently stirred for 4 hours and filtered and the filtrate is concentrated in vacuo. The residue is dissolved in methylene chloride and the solution is washed with water, dried over sodium sulphate and concentrated. The oil which remains is distilled. 18.2 g (73% of theory) of 2-chloromethyl-2-(4-chlorophenylthiomethyl)-oxirane of refractive index $n_D^{20}$ 1.5895 are obtained.

The following end products of the formula (I)

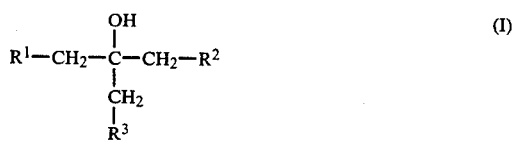
(I)

in Table 1 are obtained in a corresponding manner and by the processes according to the invention using analogous reactants and reaction conditions:

TABLE 1

| Example No. | $R^1$ | $R^2$ | $R^3$ | Melting point (°C.) or $n_D^{20}$ |
|---|---|---|---|---|
| 10 | ![triazolyl] | ![triazolyl] | -O-(2,6-dichlorophenyl) | 166 |
| 11 | " | " | -O-(4-fluorophenyl) | 90 |
| 12 | " | " | -O-(biphenyl) | 140 |
| 13 | " | " | -O-(4-CHO-phenyl) | 179 |
| 14 | " | " | -O-(2,4-dichlorophenyl) | 130 |

TABLE 1-continued
| Example No. | R¹ | R² | R³ | Melting point (°C.) or $n_D^{20}$ |
|---|---|---|---|---|
| 15 | " | 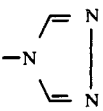 | 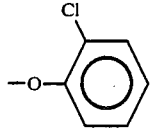 | 146 |
| 16 | " | " | 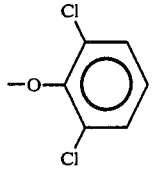 | 150 |
| 17 | " | " | 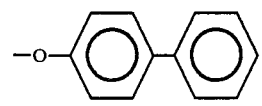 | 204 |
| 18 | " | " | 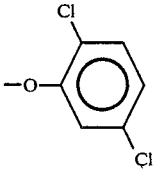 | 166 |
| 19 | 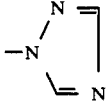 | 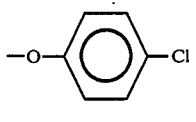 | 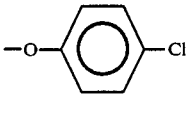 | 120 |
| 20 | 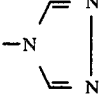 | 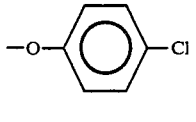 | 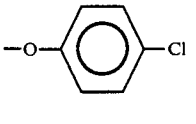 | 130 |
| 21 | 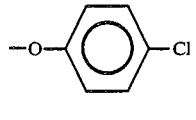 | 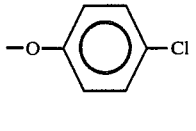 | 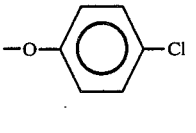 | 77 |
| 22 | 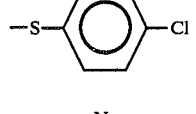 | 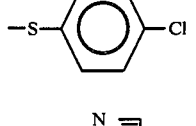 | 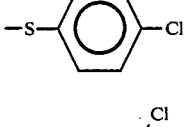 | 95 |
| 23 | 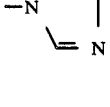 | 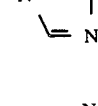 | 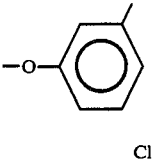 | 92 |
| 24 | 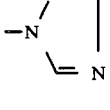 | 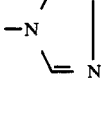 | 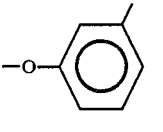 | 130 |
| 25 | 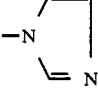 | 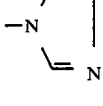 | 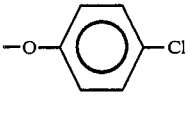 | 100 |

TABLE 1-continued

| Example No. | R¹ | R² | R³ | Melting point (°C.) or $n_D^{20}$ |
|---|---|---|---|---|
| 26 | 1,2,4-triazol-1-yl | —O—C₆H₄—Cl (p) | —S—C₆H₄—Cl (p) | 108 |
| 27 | pyrazol-1-yl | pyrazol-1-yl | —O—C₆H₄—Cl (p) | 72 |
| 28 | 1,2,4-triazol-1-yl | 1,2,4-triazol-1-yl | —O—C₆H₄—CH₃ (p) | 84 |
| 29 | 1,2,4-triazol-1-yl | 1,2,4-triazol-1-yl | —O—C₆H₃(Cl)₂ (3,4) | 158 |
| 30 | " | 1,2,4-triazol-4-yl | —O—C₆H₅ | 112 |
| 31 | " | 1,2,4-triazol-1-yl | —O—C₆H₄—OCH₃ (p) | 118 |
| 32 | " | 1,2,4-triazol-4-yl | —O—C₆H₄—OCH₃ (p) | 162 |
| 33 | " | " | —O—C₆H₃(Cl)₂ (3,4) | 188 |
| 34 | " | 1,2,4-triazol-1-yl | —N(C₂H₅)—C₆H₅ | 110 |
| 35 | " | " | —O—C₆H₃(CH₃)(SCH₃) | 70 |
| 36 | " | 1,2,4-triazol-4-yl | —O—C₆H₃(CH₃)(SCH₃) | 138 |

TABLE 1-continued

| Example No. | R¹ | R² | R³ | Melting point (°C.) or $n_D^{20}$ |
|---|---|---|---|---|
| 37 | " | -N(N=CH-N=CH) triazole | -O-C₆H₃(Cl)(Cl) (2,4-dichlorophenoxy) | 162 |
| 38 | " | -N(CH=N-CH=N) triazole | -O-C₆H₃(Cl)(Cl) (2,4-dichlorophenoxy) | 174 |
| 39 | " | -N(N=CH-N=CH) triazole | -S-C₆H₃(CH₃)(CH₃) (2,4-dimethylphenylthio) | 134 |
| 40 | " | -N(CH=N-CH=N) triazole | -N(C₂H₅)C₆H₅ | 84 |
| 41 | " | -N(N=CH-N=CH) triazole | -O-C₆H₄-CH=N-OCH₃ | 120 |
| 42 | " | " | -O-C₆H₄-O-C₆H₄-Cl | 74 |
| 43 | " | -N(CH=N-CH=N) triazole | -S-C₆H₃(CH₃)(CH₃) | 95 |
| 44 | " | -N(N=CH-N=CH) triazole | -S-C₆H₃(CH₃)(OC₂H₅) | 75 |
| 45 | " | -N(CH=N-CH=N) triazole | -S-C₆H₃(CH₃)(OC₂H₅) | 93 |
| 46 | " | -N(N=CH-N=CH) triazole | -S-C₂H₅ | 46 |
| 47 | " | " | -S-C₆H₄-Cl | 75 |

TABLE 1-continued

| Example No. | R¹ | R² | R³ | Melting point (°C.) or $n_D^{20}$ |
|---|---|---|---|---|
| 48 | " | " | —S—C₆H₅ | 70 |
| 49 | " | —N(1,2,4-triazol-1-yl) | —S—C₆H₅ | 90 |
| 50 | " | —N(1,2,4-triazol-1-yl) | —NH—C₆H₄—Cl (4-) | 116 |
| 51 | " | —NH—C₆H₄—Cl (4-) | —NH—C₆H₄—Cl (4-) | 128 |
| 52 | " | —N(1,2,4-triazol-1-yl) | —S—C₆H₄—Br (4-) | 142 |
| 53 | " | —N(1,2,4-triazol-1-yl) | " | 186 |
| 54 | " | —N(1,2,4-triazol-1-yl) | —S—C₆H₃(Cl)₂ (3,4-) | 149 |
| 55 | " | —N(1,2,4-triazol-1-yl) | " | 155 |
| 56 | " | —N(1,2,4-triazol-1-yl) | —S—C₆H₄—OCH₃ (3-) | 1.5820 |
| 57 | " | —N(1,2,4-triazol-1-yl) | " | 45 |
| 58 | " | —N(1,2,4-triazol-1-yl) | —NH—C₆H₃(Cl)₂ (2,4-) | 130 |
| 59 | " | —N(1,2,4-triazol-1-yl) | —NH—C₆H₃(Cl)₂ (2,4-) | 150 |

TABLE 1-continued

| Example No. | R¹ | R² | R³ | Melting point (°C.) or $n_D^{20}$ |
|---|---|---|---|---|
| 60 | " | -N(1,2,4-triazol-1-yl) | -NH-(3,4-dichlorophenyl) | 126 |
| 61 | " | -N(1,3,4-triazol-1-yl) | -NH-(3,4-dichlorophenyl) | 95 |
| 62 | " | -NH-(3,4-dichlorophenyl) | -NH-(3,4-dichlorophenyl) | 170 |
| 63 | " | -N(1,2,4-triazol-1-yl) | -N(CH₃)-(4-chlorophenyl) | 142 |
| 64 | " | -N(1,3,4-triazol-1-yl) | -N(CH₃)-(4-chlorophenyl) | 177 |
| 65 | " | -N(1,2,4-triazol-1-yl) | -S-(2,4-dichlorophenyl) | 90 |
| 66 | " | -N(1,3,4-triazol-1-yl) | -S-(2,4-dichlorophenyl) | 70 |
| 67 | " | -N(1,2,4-triazol-1-yl) | -NH-(2,6-dimethylphenyl) | 1.5620 |
| 68 | " | " | -NH-(3-chlorophenyl) | 1.5698 |
| 69 | " | " | -S-(4-C(CH₃)₂C₂H₅-phenyl) | 1.5600 |
| 70 | " | " | -S-(2-methoxyphenyl) | 80 |

TABLE 1-continued

| Example No. | R¹ | R² | R³ | Melting point (°C.) or $n_D^{20}$ |
|---|---|---|---|---|
| 71 | " | 1,2,4-triazol-1-yl (-N linked via N, with N=CH-N=CH pattern) | -S-C₆H₄-OCH₃ (o-methoxyphenylthio) | 108 |
| 72 | " | 1,2,4-triazol-1-yl | -S-C₆H₄-C(CH₃)₃ | 1.5608 |
| 73 | " | " | -S-C₆H₃(OCH₃)₂ (2,4-dimethoxyphenylthio) | 126 |
| 74 | " | 1,2,4-triazol-1-yl | -S-C₆H₄-C(CH₃)₂C₂H₅ | 142 |
| 75 | " | " | -S-C₆H₄-C(CH₃)₃ | 144 |
| 76 | " | " | -S-C₆H₃(OCH₃)₂ | viscous oil |
| 77 | " | 1,2,4-triazol-1-yl | -NH-C₆H₃Cl₂ (2,5-dichloroanilino) | 168 |
| 78 | " | 1,2,4-triazol-1-yl | 1,2,4-triazol-1-yl | 146 |
| 79 | " | 1,2,4-triazol-1-yl | -NH-C₆H₃Cl₂ | 108 |
| 80 | " | 1,2,4-triazol-1-yl | -S-C₆H₄-NO₂ | 150 |
| 81 | " | 1,2,4-triazol-1-yl | -S-C₆H₄-NO₂ | 188 |

TABLE 1-continued
| Example No. | R¹ | R² | R³ | Melting point (°C.) or $n_D^{20}$ |
|---|---|---|---|---|
| 82 | " | 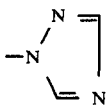 | 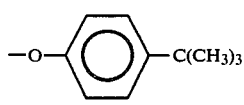 | 98 |
| 83 | " | 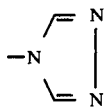 | 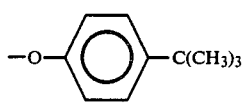 | 164 |
| 84 | " | 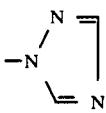 | 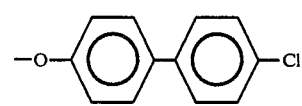 | 166 |
| 85 | " | 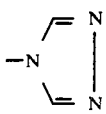 | 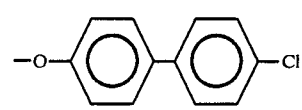 | 194 |
| 86 | " | 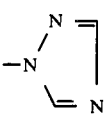 | 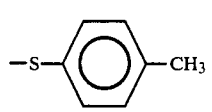 | 128 |
| 87 | " | 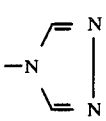 | 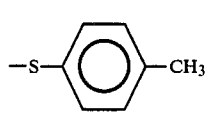 | 141 |
| 88 | " | 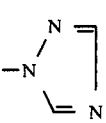 | 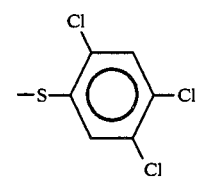 | 115 |
| 89 | " | " | 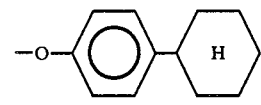 | 96 |
| 90 | " | 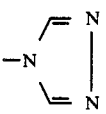 | 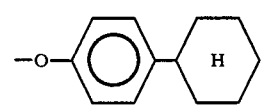 | 159 |
| 91 | " | 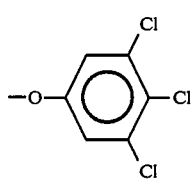 | 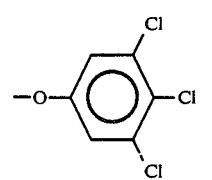 | 160 |
| 92 | " | 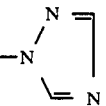 | 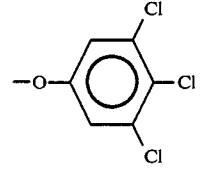 | 184 |

TABLE 1-continued

| Example No. | R¹ | R² | R³ | Melting point (°C.) or $n_D^{20}$ |
|---|---|---|---|---|
| 93 | " | 1,2,4-triazol-1-yl | 3,4,5-trichlorophenoxy | 186 |
| 94 | " | 4-acetylphenoxy | 4-acetylphenoxy | 1.5750 |
| 95 | " | 1,2,4-triazol-1-yl | 4-acetylphenoxy | 142 |
| 96 | " | 1,2,4-triazol-1-yl | 4-acetylphenoxy | 190 |
| 97 | " | 1,2,4-triazol-1-yl | 2-phenylphenoxy | 120 |
| 98 | " | 1,2,4-triazol-1-yl | 2-phenylphenoxy | 130 |
| 99 | " | 2,4,5-trichlorophenylthio | 2,4,5-trichlorophenylthio | 154 |
| 100 | " | 1,2,4-triazol-1-yl | 2,4,5-trichlorophenylthio | 80 |
| 101 | " | 1,2,4-triazol-1-yl | 4-fluorophenylthio | 114 |

TABLE 1-continued
| Example No. | R¹ | R² | R³ | Melting point (°C.) or $n_D^{20}$ |
|---|---|---|---|---|
| 102 | " |  | 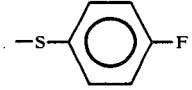 | 169 |
| 103 | " | " | 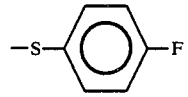 | 140 |
| 104 | " | " | 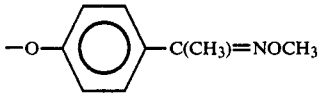 | 154 |
| 105 | " |  | 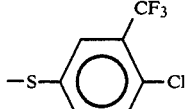 | 50 |
| 106 | " |  | 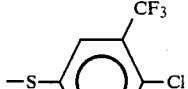 | 75 |
| 107 | " |  | —S—(CH₂)₁₁—CH₃ | 70 |
| 108 | 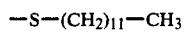 |  | 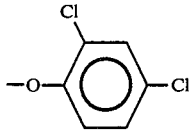 | 169 |
| 109 | " | —S—(CH₂)₁₁CH₃ | —S—(CH₂)₁₁CH₃ | 84 |
| 110 | " | 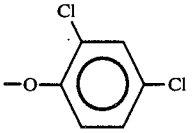 | —S—(CH₂)₁₁CH₃ | 82 |
| 111 | 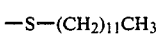 | —S—(CH₂)₁₁CH₃ | —S—(CH₂)₁₁CH₃ | 51 |
| 112 | " | 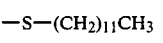 |  | 96 |
| 113 | " | 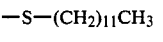 |  | 92 |

TABLE 1-continued

| Example No. | R¹ | R² | R³ | Melting point (°C.) or $n_D^{20}$ |
|---|---|---|---|---|
| 114 | " | -N(N=CH-N=CH) triazole | -O-(C₆H₃(O₂N))-O-(C₆H₃(Cl))-CF₃ | 130 |
| 115 | " | -N(N=CH-N=CH) triazole | -S-C(CH₃)₃ | 70 |
| 116 | " | -N(N=CH-N=CH) triazole | -S-C(CH₃)₃ | 91 |

The following intermediates of the formula (IV)

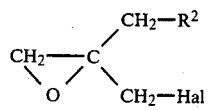

in Table 2 are obtained according to the preparation examples recited above by using analogous reactants and reaction conditions, and the general statements relating to the processes

TABLE 2

| Example No. | R² | Hal | Boiling point (°C.)/mbar or $n_D^{20}$ |
|---|---|---|---|
| (IV-5) | -O-C₆H₄-F | Cl | 100/0.2 |
| (IV-6) | -O-C₆H₃(Cl)₂ (2,4) | Cl | 145/0.1 |
| (IV-7) | -O-C₆H₃(Cl)₂ (2,3) | Cl | 155/0.3 |
| (IV-8) | -O-C₆H₄-C₆H₅ | Cl | 1.5842 |
| (IV-9) | -O-C₆H₄-CHO | Cl | 190/0.2 |
| (IV-10) | -N(C₂H₅)-C₆H₁₁ | Cl | 100/0.1 |
| (IV-11) | -S-C₆H₃(NO₂)(Cl) | Cl | 1.6270 |
| (IV-12) | -O-C₆H₄-O-C₆H₄-Cl | Cl | 1.5442 |

TABLE 2-continued

| Example No. | R² | Hal | Boiling point (°C.)/mbar or $n_D^{20}$ |
|---|---|---|---|
| (IV-13) | -O-C₆H₄-Cl | Cl | 140/0.5 |
| (IV-14) | -S-C₆H₃(CH₃)₂ | Cl | 122/0.1 |
| (IV-15) | -O-C₆H₅ | Cl | 110/0.1 |
| (IV-16) | -O-C₆H₄-OCH₃ | Cl | 120/0.2 |
| (IV-17) | -O-C₆H₃(Cl)₂ | Cl | 140/0.2 |
| (IV-18) | -O-C₆H₃(Cl)₂ | Cl | 140/0.2 |
| (IV-19) | -O-C₆H₃(CH₃)(SCH₃) | Cl | 160/0.2 |
| (IV-20) | -S-C₆H₅ | Cl | 120/0.3 |
| (IV-21) | -S-C₆H₃(CH₃)(OC₂H₅) | Cl | 138/0.1 |
| (IV-22) | -S-C₂H₅ | Cl | 1.4968 |
| (IV-23) | -N(C₂H₅)-C₆H₅ | Cl | 130/0.3 |

TABLE 2-continued

| Example No. | R² | Hal | Boiling point (°C.)/mbar or $n_D^{20}$ |
|---|---|---|---|
| (IV-24) | —NH—C₆H₄—Cl | Cl | 1,5843 |
| (IV-25) | —S—C₆H₄(OCH₃) | Cl | 160/0.3 |
| (IV-26) | —S—C₆H₄—Br | Cl | 158/0.3 |
| (IV-27) | —S—C₆H₃(Cl)(Cl) | Cl | 155/0.3 |
| (IV-28) | —S—C₆H₄—CH₃ | Cl | 1,5575 |
| (IV-29) | —S—(CH₂)₁₁—CH₃ | Cl | 1,4775 |
| (IV-30) | —S—C₆H₂(Cl)(Cl)(Cl) | Cl | 1,6065 |
| (IV-31) | —S—C₆H₃(Cl)(Cl) | Cl | 1,5951 |
| (IV-32) | —S—C₆H₄—C(CH₃)₃ | Cl | 1,5514 |
| (IV-33) | —S—C₆H₄—C(CH₃)₂C₂H₅ | Cl | 1,5408 |
| (IV-34) | —S—C₆H₄(OCH₃) | Cl | 1,5748 |
| (IV-35) | —S—C₆H₃(CH₃O)(OCH₃) | Cl | 1,5613 |
| (IV-36) | —N(CH₃)—C₆H₄—Cl | Cl | 1,5738 |
| (IV-37) | —NH—C₆H₃(Cl)(Cl) | Cl | 1,5805 |
| (IV-38) | —NH—C₆H₃(Cl)(Cl) | Cl | 1,5858 |
| (IV-39) | —NH—C₆H₃(Cl)(Cl) | Cl | 1,5940 |
| (IV-40) | —S—C₆H₄—COOH | Cl | 1,5840 |
| (IV-41) | —O—C₆H₃(O₂N)—O—C₆H₃(Cl)(CF₃) | Cl | 1,5531 |
| (IV-42) | —S—C(CH₃)₃ | Cl | 1,4871 |

The following intermediates of the formula (V)

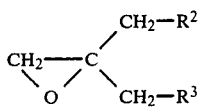

(V)

in Table 3 are obtained according to the preparation examples recited above, using analogous reactants and reaction conditions, and the general statements relating to the processes:

TABLE 3

| Example No. | R² | R³ | Melting Point (°C.) or $n_D^{20}$ |
|---|---|---|---|
| (V-2) | —O—C₆H₄—Cl | —S—C₆H₄—Cl | 1.6347 |
| (V-3) | —O—C₆H₄—Cl | —O—C₆H₄—Cl | 84 |
| (V-4) | —O—C₆H₄—C₆H₅ | —O—C₆H₄—C₆H₅ | 176 |

TABLE 3-continued

| Example No. | R² | R³ | Melting Point (°C.) or n_D^20 |
|---|---|---|---|
| (V-5) | —O—⌬ | —O—⌬ | 1.5612 |
| (V-6) | —O—⌬—OCH₃ | —O—⌬—OCH₃ | 100 |
| (V-7) | —O—⌬—Cl | —N(pyrazolyl) | 1.5590 |
| (V-8) | —O—⌬—O—⌬—Cl | —O—⌬—O—⌬—Cl | 50 |
| (V-9) | —O—⌬—Cl | —N(1,2,4-triazolyl) | 96 |

The preparation of the propene derivatives of the formulae (VIII) and (IX) which can be used as intermediates is illustrated by the following examples:

EXAMPLE α

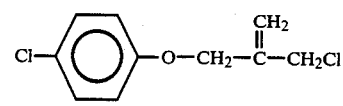
(Example VIII-1)

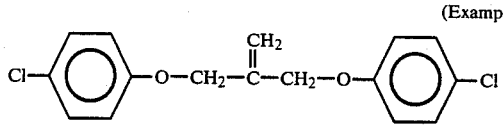
(Example IX-1)

A solution of 64.25 g (0.5 mol) of 4-chlorophenol in 100 ml of acetone is added dropwise to a mixture of 125 g (1 mol) of 3-chloro-2-chloromethyl-propene and 34.5 g (0.25 mol) of potassium carbonate in 500 ml of acetone at 60° C. The mixture is subsequently stirred at room temperatures for 18 hours and filtered and the filtrate is concentrated. The oily residue is dissolved in methylene chloride and the solution is washed once with 200 ml of 10% strength sodium hydroxide solution and then twice with in each case 500 ml of water, dried over sodium sulphate and concentrated. The oily residue is distilled. 43.2 g (41.5% of theory) of 2-chloromethyl-3-(4-chlorophenoxy)-propene (Example VIII-1) of boiling point 80° to 90° C./0.05 mbar are obtained.

10.7 g of 3-(4-chlorophenoxy)-2-(4-chlorophenoxymethyl)-propene (Example IX-1) of melting point 72° C. are obtained from the distillation residue after stirring with diisopropyl ether.

EXAMPLE β

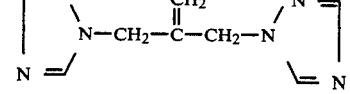
(Example VIII-2)

A mixture of 25 g (0.2 mol) of 3-chloro-2-chloromethyl-propene, 27.6 g (0.4 mol) of 1,2,4-triazole and 27.6 g (0.2 mol) of potassium carbonate in 200 ml of acetone is heated under reflux for 15 hours. After cooling, the mixture is filtered and the filtrate is concentrated in vacuo. The oily residue is chromatographed (silica gel 60, Merck, chloroform). 23 g (63% of theory) of 3-(1,2,4-triazol-1-yl)-2-(1,2,4-triazol-1-yl-methyl)-propene of melting point 52° C. are obtained.

USE EXAMPLES

The compounds shown below are used as comparison substances in the example which follows:

(A) 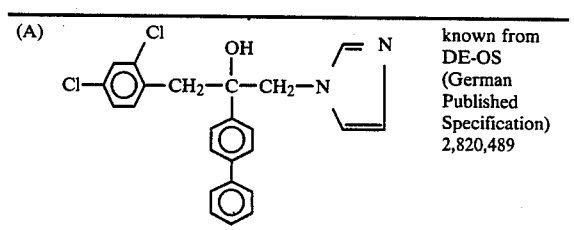 known from DE-OS (German Published Specification) 2,820,489

(B) 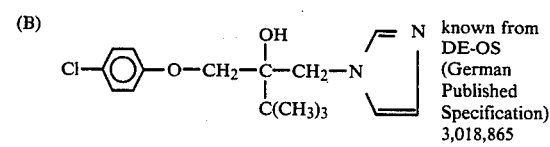 known from DE-OS (German Published Specification) 3,018,865

-continued (C) 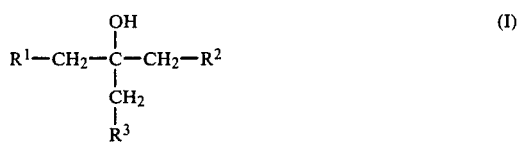  known from DE-OS (German Published Specification) 3,018,865

(D) known from DE-OS (German Published Specification) 3,018,865

(E) known from EP-OS (European Published Specification) 44,605

EXAMPLE A

Antimycotic in vivo activity (oral) in candidosis of mice

Description of the experiment:

Mice of the SPF-CF$_1$ type were infected intravenously with $1-2\times10^6$ logarithmically growing Candida cells, which are suspended in physiological sodium chloride solution. The animals were treated orally with in each case 50–100 mg/kg of body weight of the product one hour before and seven hours after the infection.

Results:

Untreated animals died 3 to 6 days after infection. The survival rate on the 6th day after infection was about 5% in the case of the untreated control animals.

In this test, for example, compounds 1, 3, 4, 8, 11 and 12 according to the invention exhibited a better action than compounds (A), (B), (C), (D) and (E) known from the prior art.

| Explanation of symbols: | | |
|---|---|---|
| + + + + + = very good action | = | 90% survivors on the 6th day after infection |
| + + + + = good action | = | 80% survivors on the 6th day after infection |
| + + + = action | = | 60% survivors on the 6th day after infection |
| + + = slight action | = | 40% survivors on the 6th day after infection |
| + = trace of action | = | 40% survivors on the 6th day after infection |
| n.a. = no action | | |

TABLE A

| Antimycotic in vivo activity (oral) in candidosis of mice | |
|---|---|
| Active compound | Action |
| (A) (known) | n.a. |
| (B) (known) | n.a. |
| (C) (known) | n.a. |
| (D) (known) | n.a. |
| (E) (known) | n.a. |
| Compounds according to the preparation examples: | |
| 1 | + + + + + |
| 3 | + + + + + |
| 4 | + + + |
| 8 | + + + + + |
| 11 | + + + + + |
| 12 | + + + + + |
| Example B/formulations | |

TABLE A-continued

| Antimycotic in vivo activity (oral) in candidosis of mice | |
|---|---|
| 1. Solution: | |
| Active compound according to the formula (I) | 10 g |
| Alcohol, pure (96% strength) | 300 g |
| Isopropyl myristate | 526 g |
| | 836 g |
| 2. Cream: | |
| Active compound according to the formula (I) | 10 g |
| Arlacel 60 | 20 g |
| (Sorbitan monostearate) Tween 60 | 15 g |
| Polyoxyethylene(2)-sorbitan monostearate | |
| Spermaceti, synthetic | 30 g |
| (Mixture of esters of saturated $C_{14}$–$C_{18}$ fatty acids and $C_{14}$–$C_{18}$ fatty alcohols) | |
| Lanette O | 100 g |
| (Mixture of cetyl alcohol and stearyl alcohol) | |
| Entanol G | 135 g |
| (2-Octyl-dodecanol) | |
| Benzyl alcohol | 10 g |
| Water, demineralised | 680 g |
| | 1,000 g |

We claim:

1. A substituted tert.-butanol derivative of the formula $$R^1-CH_2-\underset{\underset{\underset{R^3}{|}}{CH_2}}{\overset{\overset{OH}{|}}{C}}-CH_2-R^2 \quad (I)$$

in which

R$^1$ and R$^2$ are identical or different and represent imidazol-1-yl, 1,2,4-triazol-1-yl; 1,2,4-triazol-4-yl or pyrazol-1-yl and R$^3$ represents phenoxy, phenylthio, phenylimino or phenyl-N-alkyl-amino with 1 to 4 carbon atoms in the alkyl part, each radical being optionally monosubstituted or polysubstituted by identical or different substituents, said substituents or phenyl in each case being: halogen, alkyl with 1 to 5 carbon atoms, alkoxy and alkylthio with in each case 1 to 4 carbon atoms; halogenoalkyl, halogenoalkoxy and halogenoalkylthio with in each case 1 to 4 carbon atoms and 1 to 5 identical or different halogen atoms; cycloalkyl with 5 or 6 carbon atoms; nitro, cyano, hydroxycarbonyl, alkylcarbonyl or alkoxycarbonyl with in each case 1 to 4 carbon atoms in the alkyl part, phenyl or phenoxy which is optionally monosubstituted or polysubstituted by identical or different substituents selected from the group consisting of halogen, nitro, trifluoromethyl and alkyl, with 1 to 2 carbon atoms, the aldehyde group or the oxime or hydroxyiminoethyl or methoxyiminomethyl radical.

2. A substituted tert.-butanol derivative of claim 1, of the formula (I)

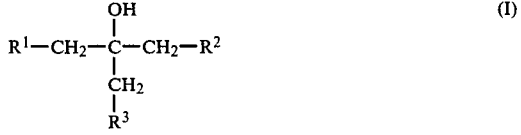

in which $R^1$ and $R^2$ are identical or different and represent imidzol-1-yl; 1,2,4-triazol-1-yl; 1,2,4-triazol-4-yl or pyrazol-1-yl, and $R^3$ represents phenoxy, phenylthio, phenylamino or phenyl-N-alkyl-amino with 1 or 2 carbon atoms in the alkyl part, each radical optionally being mono-substituted or di- or tri-substituted by identical or different substituents, said substituents on the phenyl in each case being: fluorine, chlorine, bromine, methyl, ethyl, isopropyl, tert.-butyl, 2-methyl-but-2-yl, methoxy, ethoxy, methylthio, trifluoromethyl, trifluoromethoxy, trifluoromethylthio, cyclohexyl, nitro, cyano, hydroxycarbonyl, methylcarbonyl, methoxycarbonyl, ethoxycarbonyl, or phenyl or phenoxy, in each case optionally mono-substituted or di- or tri-substituted by identical or different substituents selected from the group consisting of chlorine, nitro, trifluoromethyl and methyl, or the aldehyde group, hydroxyiminoethyl or methoxyiminomethyl.

3. A compound of claim 1 which is 2-(4-Chlorophenoxymethyl)-1,3-di-(1,2,4-triazol-1-yl)-2-hydroxypropane.

4. A compound of claim 1 which is 2-(2,4-Dichlorophenoxymethyl)-1,3-di(1,2,4-triazol-1-yl)-2-hydroxypropane.

5. A compound of claim 1 which is 2-(2,4-Dichlorophenoxymethyl)-2-hydroxy-1-(1,2,4-triazol-1-yl)-3-(1,2,4-triazol-4-yl)-propane.

6. A compound of claim 1 which is 2-(4-Chlorophenylthiomethyl)-1,3-di-(1,2,4-triazol-1-yl)-2-hydroxypropane.

7. A compound of claim 1 which is 1,3-Di-(1,2,4-triazol-1-yl)-2-(4-fluoro-phenoxymethyl)-2-hydroxypropane.

8. A compound of claim 1 which is 1,3-Di-(1,2,4-triazol-1-yl)-2-(4-phenylphenoxymethyl)-2-hydroxypropane.

9. A pharmaceutical composition containing as an active ingredient an antimycotically effective amount of a compound of claim 1 in admixture with an inert pharmaceutical carrier.

10. A pharmaceutical composition of claim 9 in the form of a sterile or physiologically isotonic aqueous solution.

11. A composition according to claim 9 containing from 0.5 to 90% by weight of the said active ingredient.

12. A medicament in dosage unit form comprising an antimycotically effective amount of a compound of claim 1 and an inert pharmaceutical carrier.

13. A medicament of claim 12 in the form of tablets, pills, dragees, capsules, ampoules or suppositories.

14. A method of combatting mycosis in warm-blooded animals which comprises administering to said animals an antimycotically effective amount of an active compound according to claim 1 either alone, or in admixture with a diluent or in the form of a medicament.

15. A method according to claim 14 in which the active material is administered in an amount of about 50 to about 300 mg/kg body weight per day.

16. A method according to claim 14 in which the active compound is administered orally or parenterally.

* * * * *

UNITED STATES PATENT AND TRADEMARK OFFICE
CERTIFICATE OF CORRECTION

PATENT NO. : 4,621,095

DATED : November 4, 1986

INVENTOR(S) : Erik Regel, et al.

It is certified that error appears in the above-identified patent and that said Letters Patent is hereby corrected as shown below:

| | |
|---|---|
| Col. 10, line 61 | Delete "anims" and substitute --animals-- |
| Col. 44, line 38 | Delete "phenylimino" and substitute --phenylamino-- |
| Col. 44, line 42 | Delete "or" and substitute --on-- |
| Col. 45, line 2 | Delete "imidzol" and substitute --imidazol-- |

Signed and Sealed this

Twenty-fourth Day of March, 1987

Attest:

DONALD J. QUIGG

Attesting Officer    Commissioner of Patents and Trademarks